United States Patent [19]
Sekimoto et al.

[11] Patent Number: 5,767,682
[45] Date of Patent: Jun. 16, 1998

[54] ELECTRIC CONDUCTIVITY MEASUREMENT CIRCUIT AND PROBE

[75] Inventors: Michio Sekimoto, Sagamihara; Satoshi Suyama, Hadano, both of Japan

[73] Assignee: The Tsurumi-Seiki Co., Ltd., Yokohama, Japan

[21] Appl. No.: 546,409

[22] Filed: Oct. 20, 1995

[30] Foreign Application Priority Data

Jun. 28, 1995 [JP] Japan ................................. 7-161944

[51] Int. Cl.$^6$ .............................. G01N 27/06; G01R 27/22
[52] U.S. Cl. ........................ 324/445; 324/727; 324/204
[58] Field of Search ........................ 324/439, 442, 324/445, 654, 693, 709, 710, 722, 724, 204

[56] References Cited

U.S. PATENT DOCUMENTS

| | | | |
|---|---|---|---|
| 3,292,077 | 12/1966 | Sloughter | 324/445 |
| 3,906,353 | 9/1975 | Murdock | 324/442 |
| 4,220,920 | 9/1980 | Gross | 324/442 |
| 5,157,332 | 10/1992 | Reese | 324/445 |
| 5,341,102 | 8/1994 | Akiyama et al. | 324/445 |
| 5,455,513 | 10/1995 | Brown et al. | 324/445 |

FOREIGN PATENT DOCUMENTS 5188030  7/1993  Japan.

*Primary Examiner*—Michael Brock
*Attorney, Agent, or Firm*—John P. White; Cooper & Dunham LLP

[57] ABSTRACT

In an electric conductivity measurement circuit according to the invention, there are provided first and second cores for forming a closed flux loop in a liquid whose electric conductivity is to be measured, a first coil is wound on the first core, and a second coil is wound on the second core in a direction opposite to the direction of the winding of the first coil, a closed circuit includes the first and second coils, a reference resistor Rr and switch means, and the switch means is periodically turned on and off to periodically incorporate the reference resistor Rr in the closed circuit, thereby calculating the electric conductivity of the liquid by comparing a voltage induced at the second coil where the reference resistor Rr is incorporated in the closed circuit, with a voltage induced at the second coil where the reference resistor Rr is not incorporated in the closed circuit.

3 Claims, 7 Drawing Sheets

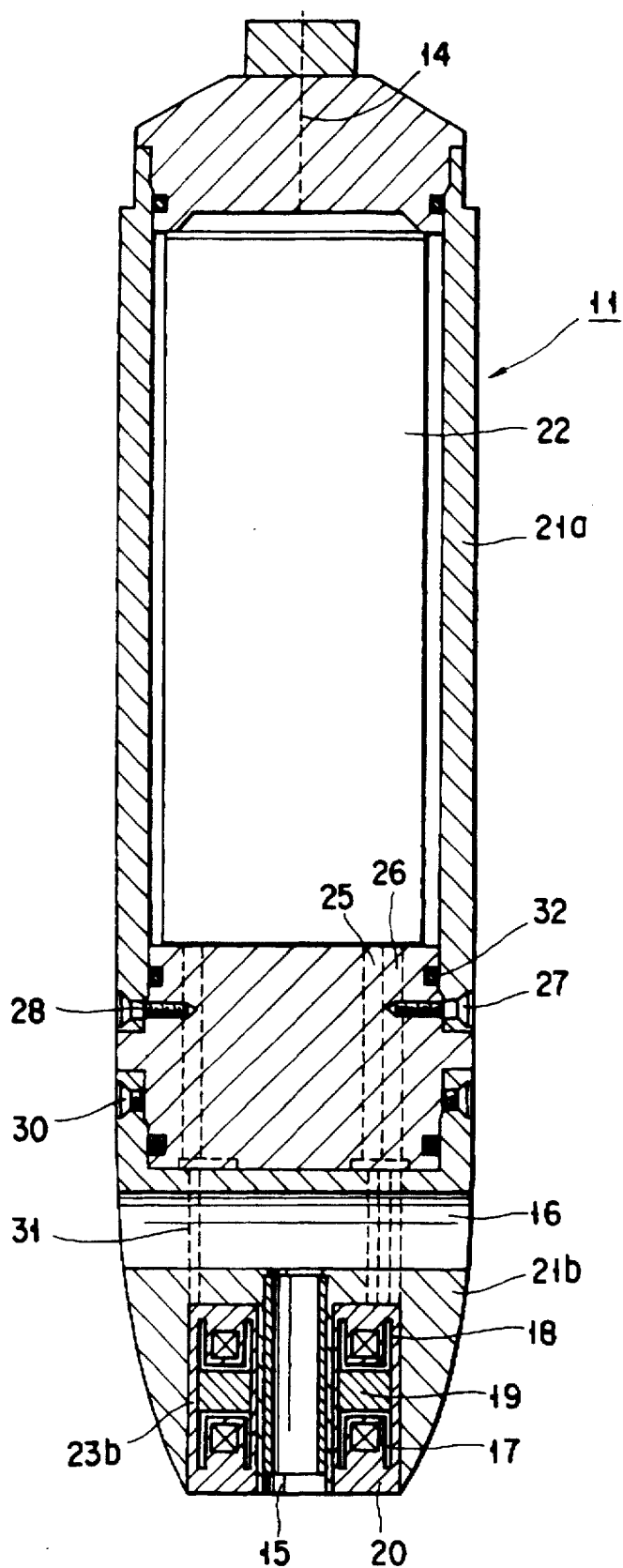
F I G. 1

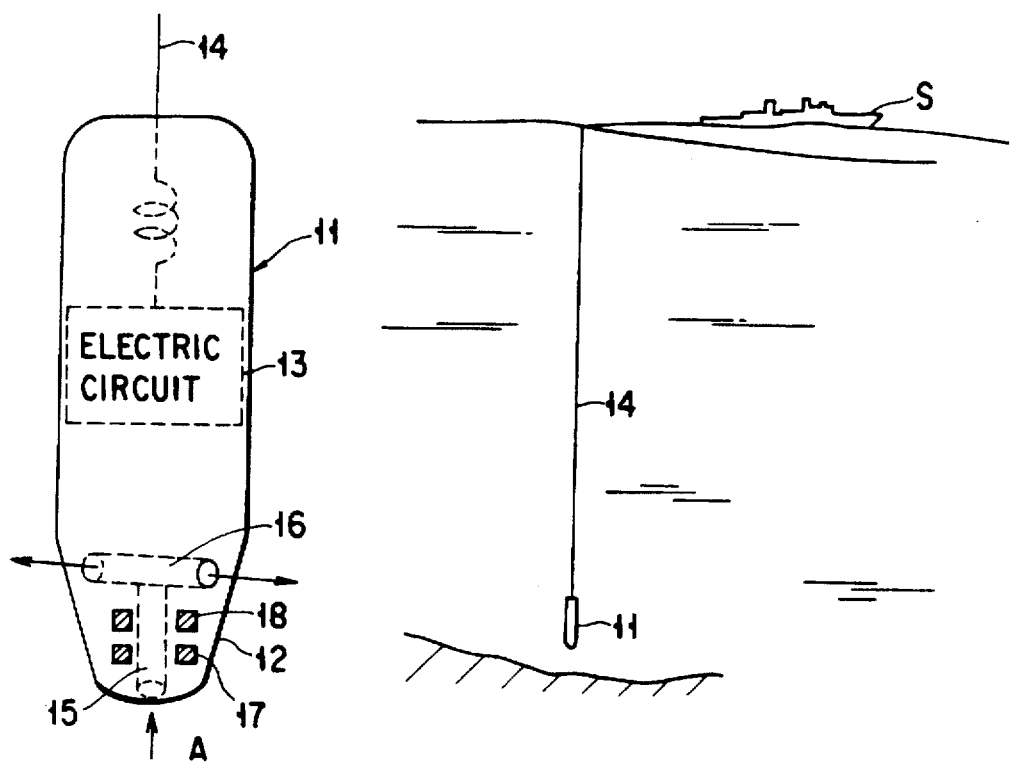
FIG. 3
FIG. 4
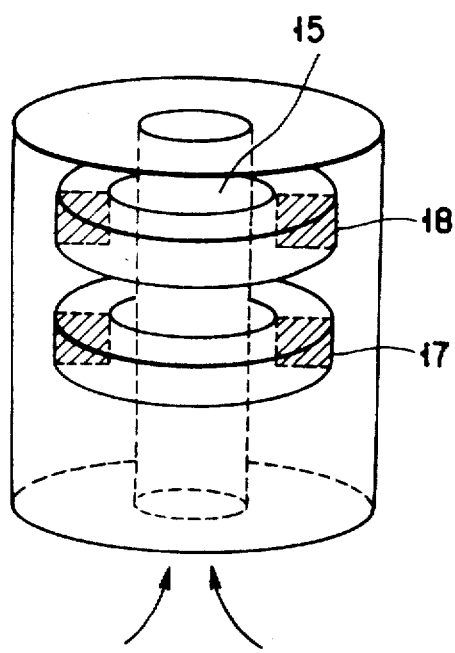
FIG. 5

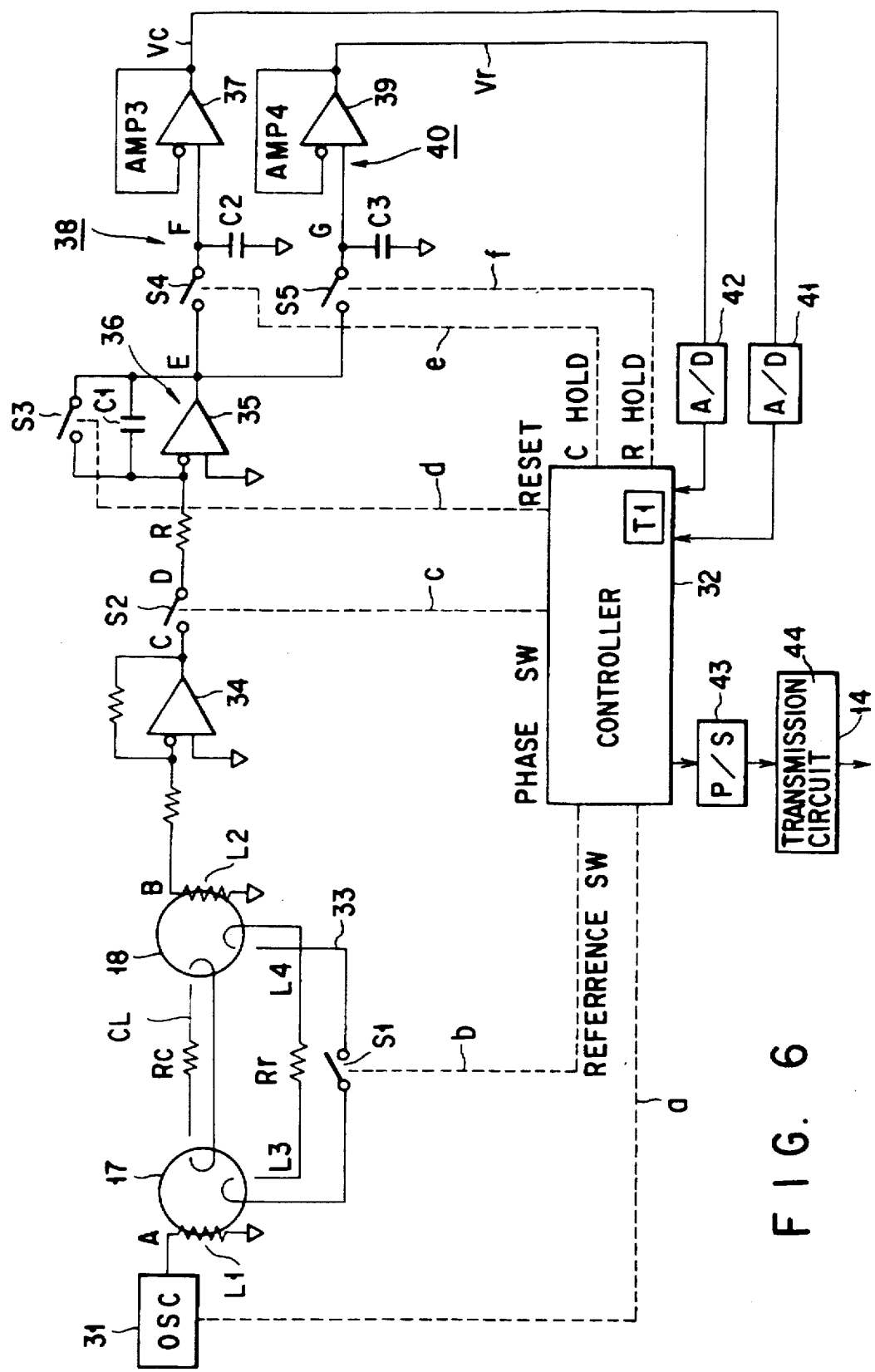
F I G. 6

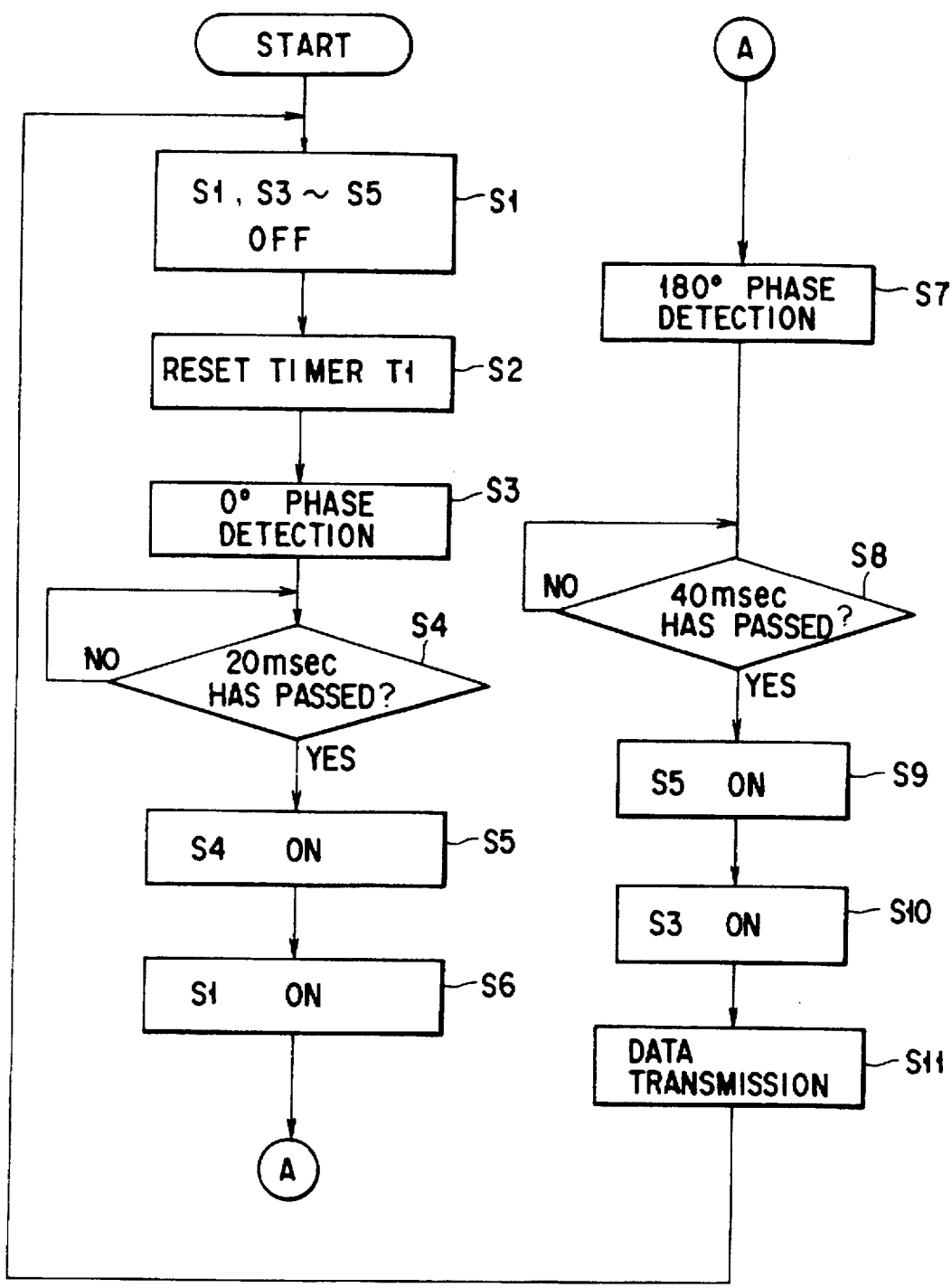
F I G. 7

ELECTRIC CONDUCTIVITY MEASUREMENT CIRCUIT AND PROBE

BACKGROUND OF THE INVENTION

1. Field of the Invention

This invention relates to a measurement circuit and probe for use in an ocean data automatic measurement apparatus, capable of automatically measuring the electric conductivity of the ocean in the vertical direction.

2. Description of the Related Art

There is a measurement apparatus widely known as "XBT" (expendable bathy thermograph), which continuously measures real-time temperatures of the ocean in the vertical direction, using a probe with a water temperature sensor built therein. Specifically, the measurement is performed by throwing the probe into the ocean from a cruising surveying ship, allowing free fall of the same in the ocean in the vertical direction, continuously measuring real-time temperatures of the ocean, and transmitting a signal indicative of the measured real-time temperatures to the surveying ship through transmission wires (made of e.g. extremely thin electric wires). The obtained water temperature data are used as important ocean observation data. After predetermined water temperature data are obtained using the XBT probe thrown into the ocean, the transmission wires are cut and cast away in the ocean together with the probe.

Further, there is a measurement apparatus generally known as "CTD" (conductivity temperature depth), which measures the electric conductivity of sea water as well as its temperature, in order to observe various phenomena of the ocean. This apparatus has a probe with a water temperature sensor, an electric conductivity sensor and a depth sensor built therein. The probe is thrown from a surveying ship into the ocean by means of a cable, and real-time temperatures, electric conductivities and depths of the ocean are transmitted to a surveying ship by means of the cable. The relationship between the water temperature and electric conductivity of the ocean and the depth of the same is displayed or printed.

In addition, a CTD measurement apparatus is known which has a memory built in a probe for storing measured water temperatures and electric conductivities. In this case, the probe is hung by a rope, etc., and is thrown into the ocean and raised therefrom, thereby reading data stored in the memory. The read data concerning the relationship between the temperature, electric conductivity, etc. and the depth are displayed or printed.

In the case of the first-mentioned CTD measurement apparatus, ocean data concerning the temperature, electric conductivity, etc. of the ocean is transmitted to the surveying ship via the cable. Therefore, real-time ocean data can be obtained. However, the surveying ship cannot cruise with the cable trailed. In other words, the surveying ship must be anchored until the observation is finished. Accordingly, a great amount of fee is required for the anchorage of the ship, and also a great amount of time is required for the observation. Moreover, extra fee and stuff are necessary to provide a dedicated winch.

On the other hand, in the case of the latter CTD measurement apparatus, the ocean data cannot be output unless the probe is raised from the ocean. Therefore, real-time ocean data cannot be obtained.

In light of the above, there has been a demand for a CTD measurement apparatus capable of measuring the real-time temperature and electric conductivity of the ocean while the surveying ship is cruising.

In such a CTD measurement apparatus, wires (e.g. two extremely thin electric wires) are connected to a probe, and the probe and the wires must be cast in the ocean after the probe is made to free-fall to a target depth. Therefore, it is necessary to use a cheap probe, desirably a cheap and accurate probe.

Japanese Patent Application KOKAI Publication No. 5-188030 discloses a cheap thrownaway-type ocean data automatic measurement apparatus with a probe of high accuracy and resolution. This apparatus is of a so-called electrode type, in which the resistance between electrodes is measured to obtain ocean data.

In the electrode type apparatus, however, a great amount of time is required until the electrodes are adapted to sea water after the probe is thrown into the sea. Therefore, the reliability of measurement data concerning the electric conductivity of sea water in the vicinity of the sea surface is inevitably low.

In addition, since in the electrode type apparatus, sea water is used as a ground terminal, noise or an error may well occur in the measurement data.

SUMMARY OF THE INVENTION

The object of the invention is to provide an electric conductivity measurement circuit and probe capable of preventing such a delay in the start of measurement as is found in an electrode type apparatus until the surfaces of electrodes employed therein are adapted to a liquid to be examined, in order to measure the electric conductivity of the liquid with high accuracy.

To attain the object, there is provided an electric conductivity measurement circuit comprising:

first and second cores for forming a closed flux loop in a liquid whose electric conductivity is to be measured;

a first coil wound on the first core, and a second coil wound on the second core in a direction opposite to the direction of the winding of the first coil;

an oscillator for supplying voltage pulses to the first coil of the first core;

a phase detection circuit for detecting the phase of a voltage induced at the second coil of the second core;

a closed circuit including a third coil wound on the first core, a fourth coil wound on the second core in a direction opposite to the direction of the winding of the third coil, a reference resistor Rr and switch means;

an integration circuit for integrating outputs from the phase detection circuit;

first and second sampling hold circuits for holding output signals from the integration circuit, respectively; and control means for periodically turning on and off the switch means, thereby detecting the phase of a voltage induced at the second coil, in synchronism with the trailing edge of each of the voltage pulses while the switch means is in an off period, integrating voltages, induced at the second coil, by means of the integration circuit, holding in the first sample hold circuit a voltage Vc output from the integration circuit as a result of integration performed until the off period terminates, detecting the phase of a voltage induced at the second coil, in synchronism with the trailing edge of each of the voltage pulses while the switch means is in an on period, integrating voltages, induced at the second coil in the off and on periods, by means of the integration circuit, holding in the second sample hold circuit a voltage Vr output from the integration circuit as a result of integration performed until the on period terminates, and calculating the electric conductivity Kc of the liquid using the following equation:

$$Kc=(S/Rr)(Vc/Vr)$$

where S represents a cell constant which depends upon the configuration of a cell.

By virtue of the above structure, the invention provides an electric conductivity measurement circuit and probe which does not require temperature compensation and can prevent such a delay in the start of measurement as is found in an electrode type apparatus until the surfaces of electrodes employed therein are adapted to a liquid to be examined, in order to measure the electric conductivity of the liquid with high accuracy.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIG. 1 is a cross sectional view, showing a probe according to the embodiment of the invention;

FIG. 3 is a view, showing the appearance of the probe of FIG. 1;

FIG. 4 is a view, useful in explaining a method for measuring the electric conductivity by throwing down the probe;

FIG. 5 is a view, showing first and second cores provided in a tip portion of the probe;

FIG. 6 is a circuit diagram, showing an electric conductivity measurement circuit incorporated in the probe;

FIG. 7 is a flowchart, useful in explaining the operation of the embodiment;

DETAILED DESCRIPTION OF THE PREFERRED EMBODIMENTS

Figure 2:
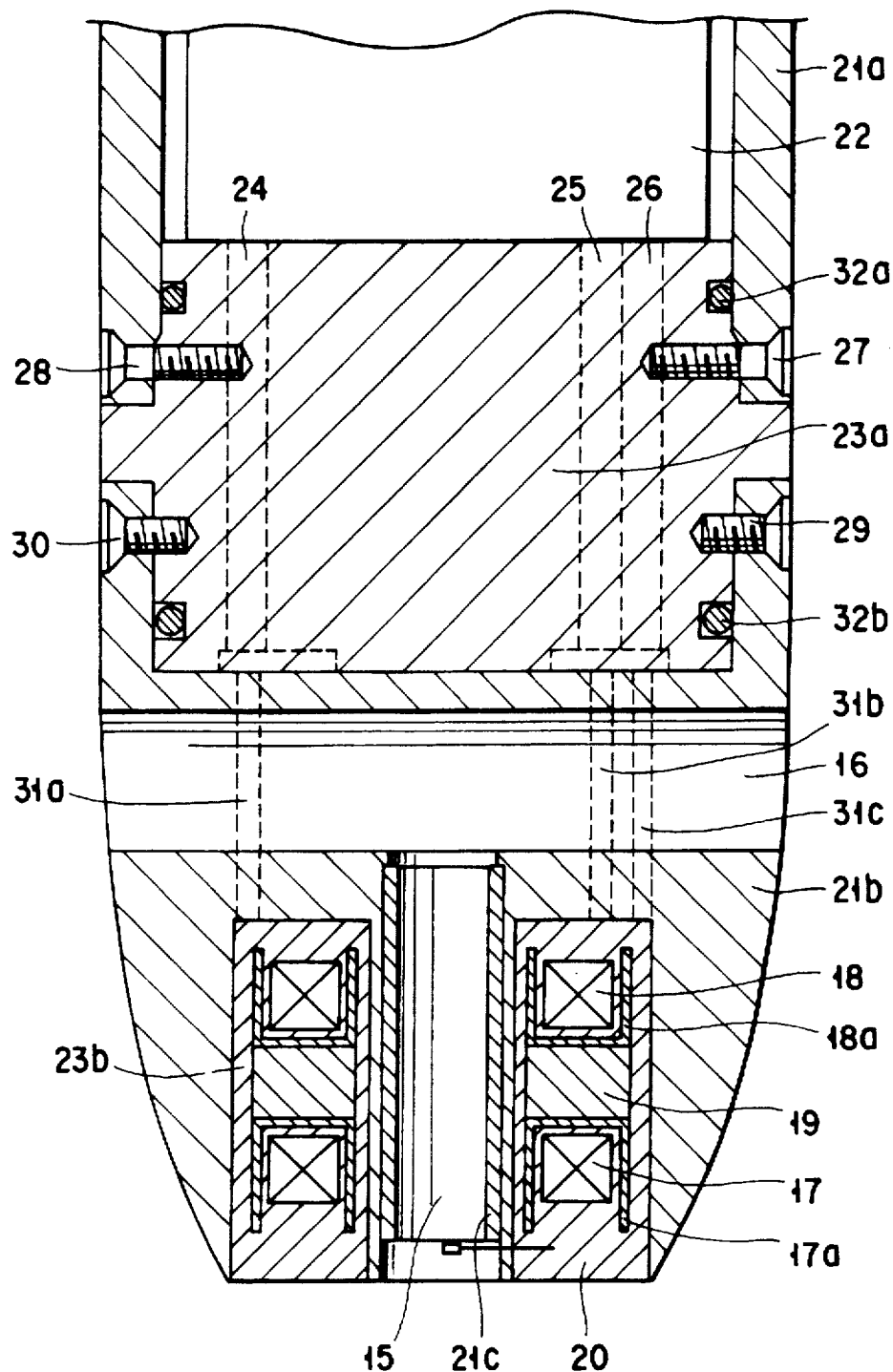
FIG. 2 is a cross sectional view, showing an essential part of the probe of FIG. 1.

The embodiment of the invention will be explained with reference to the accompanying drawings. Referring first to FIG. 3, the appearance of a probe for measuring the electric conductivity will be explained. In FIG. 3, reference numeral 11 denotes a probe. The probe 11 has a tip portion 12 in the shape of a cone, and a cylindrical portion 13 formed integral with the tip portion 12 as one body by means of a resin.

The cylindrical portion 13 houses an electric circuit, which will be explained later with reference to FIG. 4. A extremely thin wire 14 extends from the inside of the probe to the outside for transmitting Kc data concerning the electric conductivity output from the electric circuit at an interval of 40 msec. The wire 14 is wound in the probe 11 before the probe 11 is thrown into the ocean, and unwound while the probe 11 is dropping. The wire 14 has an end connected to the electric circuit and the other end connected to a personal computer (not shown) installed in a surveying ship (indicated by reference symbol S in FIG. 4).

An axial cylindrical passage 15 is formed in the tip portion 12 for introducing sea water to be measured. This passage 15 communicates with a through hole 16 which extends perpendicular to the axis of the probe 11. Thus, as the probe 11 drops, sea water flowing into the probe through the passage 15 from the direction indicated by arrow A is discharged to the outside through the through hole 16.

First and second cores 17 and 18 are provided around the passage 15, axially separated from each other, as shown in FIG. 5.

Referring then to FIGS. 1 and 2, the structure of the probe 11 will be explained in detail. In FIG. 1, reference numeral 21 denotes a probe body having an upper cylinder portion 21a and a lower cone portion 21b, which are formed of a resin integral as one body. The cylinder portion 21a houses a printed board 22 with an electric circuit shown in FIG. 4. The cylindrical passage 15 for introducing sea water to be examined extends along the axis of the cone portion 21b. The hole 16 communicates with the passage 15 at right angles.

A core receiving portion 23b with an annular hole formed therein is provided around the passage 15. As is shown in FIG. 2, the first core 17 is received in an annular magnetic shielding member 17a with an opening directed downward, while the second core 18 is received in an annular magnetic shielding member 18a with an opening directed upward. The magnetic shielding members 17a and 18a are opposed to each other with a spacer interposed therebetween. An epoxy resin 20 is filled in the core receiving portion 23b to fix the first and second cores 17 and 18, the spacer 19 and the magnetic shielding members 17a and 18b.

A cylindrical borosilicate glass member 21c having an extremely low thermal expansion coefficient is provided on the inner periphery of the passage 15 for preventing the resin cone portion 21b from being deformed due to a change in temperature or pressure to fix the inner diameter of the passage 15.

A cylindrical weight member 23a formed of a metal is interposed between the cylinder portion 21a and the cone portion 21b. Through holes 24 to 26 are formed in the weight member 23a along the axis of the probe 11 for inserting therein electric wires. Although FIG. 2 illustrates the holes 25 and 26 as if they contact each other, these holes are actually separated in the fore and aft direction of the drawing sheet.

The weight member 23a is fixed in a liquid tight manner by means of the cylinder portion 21a and screws 27 to 30. Reference signs 32a and 32b denote O-rings.

Further, through holes 31a to 31c are formed in those portions of the cone portion 21b which correspond to the through holes 24 to 26.

The electric wires of the printed board 22 are electrically connected to first and second coils L1 and L2 respectively wound on the first and second cores 17 and 18, and third and fourth coils L3 and L4 which will be explained later.

Referring then to FIG. 6, the electric circuit mounted on the printed board 22 will be explained. The first coil L1 serving as a primary coil is wound on the first core 17. The first coil L1 has an end connected to a GND circuit, and the other end connected to an oscillator 31 for outputting a high frequency pulse voltage A, shown in FIG. 8. The frequency of the high frequency pulse voltage is 12.8 KHz. A reference phase line a is connected between the oscillator 31 and the controller 32.

Figure 8:
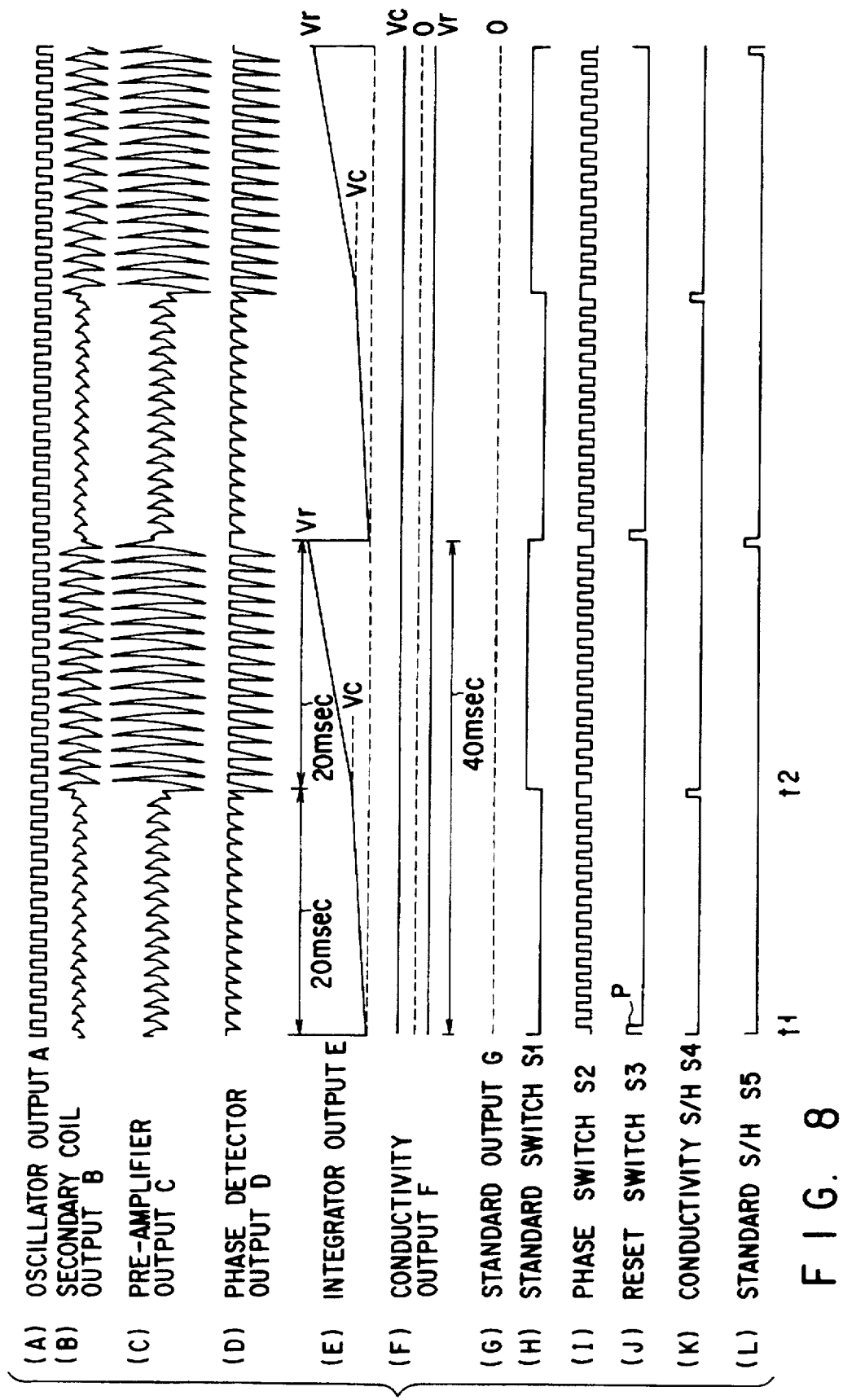
FIG. 8 is a timing chart, useful in explaining the operation of the embodiment.

The third coil L3 is formed by winding an electric wire 33 by one turn on the first core 17, while the fourth coil L4 is formed by winding the electric wire 33 by one turn on the second core 18 in a direction opposite to the direction of the winding of the third coil L3. The third and fourth coils are connected to each other via a reference resistor Rr and a switch S1, thereby forming a closed loop. The switch S1 consists of a semiconductor switch to be turned on/off in response to a control signal b output from the controller 32. As is shown in FIG. 8, the on/off states of the switch S1 are alternated in units of 20 msec. The reference resistor Rr needs no temperature compensation, and its equivalent conductance Kr is S/Rr (S represents a cell constant).

In FIG. 6, the first and second cores 17 and 18 and a resistor Rc interposed therebetween form a loop CL. The resistor Rc indicates the equivalent resistance of sea water flowing into the passage 15 of the probe 11, and is equal to S/Kc.

The second coil L2 wound on the second core 18 serves as a secondary coil. The coil L2 has an end connected to the GND circuit, and outputs from the other end a secondary coil output B as shown in FIG. 8.

The voltage induced at the second coil L2 is amplified by a pre-amplifier 34. The output of the pre-amplifier 34 is supplied, as a pre-amplifier output C as shown in FIG. 8, to an integrator 36 which consists of an operational amplifier 35, a capacitor C1 and a resistor R, via a switch S2. A switch S3 is interposed between the input and output terminals of the operational amplifier 35 for resetting a voltage charged in the capacitor C1.

The switch S2 is a phase-detecting switch to be closed in synchronism with the leading or trailing edge of the oscillator output A shown in FIG. 8. When the switch S2 is closed in synchronism with the leading edge of the oscillator output, it detects a phase of "0" degree. On the other hand, when the switch S2 is closed in synchronism with the trailing edge of the oscillator output, it detects a phase of "180" degrees. The output of the switch S2 is output as a phase detection output D. The on/off control of the switch S2 is performed in response to a control signal c output from the controller 32.

The on/off control of the switch S3 is performed in response to a control signal d output from the controller 32. As is shown in FIG. 8, the switch S3 is turned on for an instant at intervals of 40 msec.

The output voltage E of the integrator 36 is supplied to a sampling hold circuit 38 constituted by a switch S4 and a buffer 37, and also to a sampling hold circuit 40 constituted by a switch S5 and a buffer 39.

An output terminal F between the switch S4 and the buffer 37 is connected to the GND circuit via a capacitor C2.

An output terminal G between the switch S5 and the buffer 39 is connected to the GND circuit via a capacitor C3.

The on/off control of the switch S4 is performed in response to a control signal e output from the controller 32. As is shown in FIG. 8, the switch S4 is turned on for an instant immediately before the switch S1 is turned on 20 msec. after the output of a reset pulse P from the switch S3. As a result, while the switch S1 is in the off-state (in the open state), a voltage Vc obtained by integration by the integrator 36 can be kept in the buffer 37.

The on/off control of the switch S5 is performed in response to a control signal f output from the controller 32. As is shown in FIG. 8, the switch S5 is turned on for an instant after 40 msec. elapses from the output point of the pulse P and immediately before the output point of the next reset pulse P; As a result, while the switch S1 is shifted from the off-state (the open state) to the on-state (the closed state), a voltage Vr obtained by integration by the integrator 6 can be kept in the buffer 39.

The voltages Vc and Vr kept in the buffers 37 and 39 are converted to digital data by means of A/D converters 41 and 42, respectively, and then supplied to the controller 32.

The controller 32 is further connected to a transmission circuit 44 via a P/S (parallel/serial) conversion circuit 43 for calculated electricity conductivity data to serial data. The transmission circuit 44 sequentially transmits, via the wire 14 at intervals of 40 msec., electric conductivity data concerning a to be examined liquid, to a personal computer installed in a survey ship S.

The controller 32 comprises, for example, a 4-bit microprocessor. The controller 32 performs on/off control of the switches S1–S5 using the control signals b–f based on the reference phase signal a. Further, the controller 32 calculates the electric conductivity Kc of the to-be-examined liquid (i.e. sea water flowing through the passage 15) on the basis of voltages Vc and Vr input through the A/D converters 41 and 42 and the reference resistor Rr, using the following equation:

$$Kc=(S/Rr)*(Vc/Vr)$$

The operation of the embodiment of the invention constructed as above will be explained. Referring first to the flowchart of FIG. 7, the overall operation will be roughly explained. When the surveying ship S has reached a region in which the electric conductivity Kc is to be examined, the probe 11 is taken out of a canister (not shown), and dropped into the sea after the power supply (not shown) of the controller 32 is turned on. Upon turning on the power supply, the switches S1, S2 to S5 are turned off (step S1). Then, a timer T1 is reset (step S2).

Subsequently, the switch S2 is closed when the phase of the output of the oscillator 31 is "0" degree, to thereby perform "0"° phase detection (step S3).

Then, it is determined on the basis of the timer T1 whether or not 20 msec. has elapsed (step S4). If it is determined that 20 msec. has elapsed, the switch S4 is closed to hold, in the sampling hold circuit 38, the voltage Vc obtained by integration by the integrator 36 (step S5).

The switch S1 is closed and the electric wire 33 is incorporated in the circuit (step S6).

Thereafter, the switch S2 is closed when the phase of the output of the oscillator 31 is 180°, to thereby perform "180"° phase detection (step S7).

It is determined on the basis of the timer T1 whether or not 40 msec. has elapsed (step S8).

If it is determined in the step SB that 40 msec. has elapsed, the switch S5 is closed to hold, in the sampling hold circuit 40, the voltage Vr obtained by integration by the integrator 36 (step S9).

Then, the switch S3 is closed and the voltage integrated by the integrator 36 is cleared (step S10), thereby calculating the electric conductivity and transmitting a calculation result to the personal computer in the survey ship S via the wire 14 (step S11).

The operation of the invention will be explained in detail. The probe 11 thrown into the ocean continues to free-fall because of its own weight, while it unwinds the wire 14 contained therein. Since the probe 11 houses the metal weight member 23, it free-falls with the cone portion 21b directed downward.

Accordingly, sea water flows into the cone portion 21b through the passage 15, and discharges through the hole 16 in a lateral direction.

The measurement circuit according to the invention calculates the electric conductivity Kc of sea water between the first and second cores 17 and 18 in the passage 15.

As is shown in FIG. 8, the switch S1 is repeatedly turned on and off at intervals of 20 msec.

First, the operation of the circuit will be explained, which is performed from a time point t1 to a time point t2 for which the switch S1 is in the off state. Since the switch S1 is in the off state, the electric wire 33 does not form a closed loop.

Therefore, the first coil L1 wound on the first core 17 is supplied with a high frequency pulse voltage A of a waveform as shown in FIG. 8 from the oscillator 31.

Since the voltage applied to the first coil L1 varies, the flux density transmitted from the first core 17 to the second core 18 varies. As a result, an output voltage B as shown in FIG. 8 is induced at the second coil L2 wound on the second core 18.

The output voltage B increases in proportion to the electric conductivity Kc of the resistor Rc, since the flux density transmitted from the first core 17 to the second core 18 increases in accordance with the electric conductivity of a medium which exists between the first and second cores 17 and 18, i.e. the electric conductivity of sea water in the passage 15.

Thus, the electric conductivity Kc of sea water in the passage 15 can be measured by measuring the output voltage B.

Figure 9:
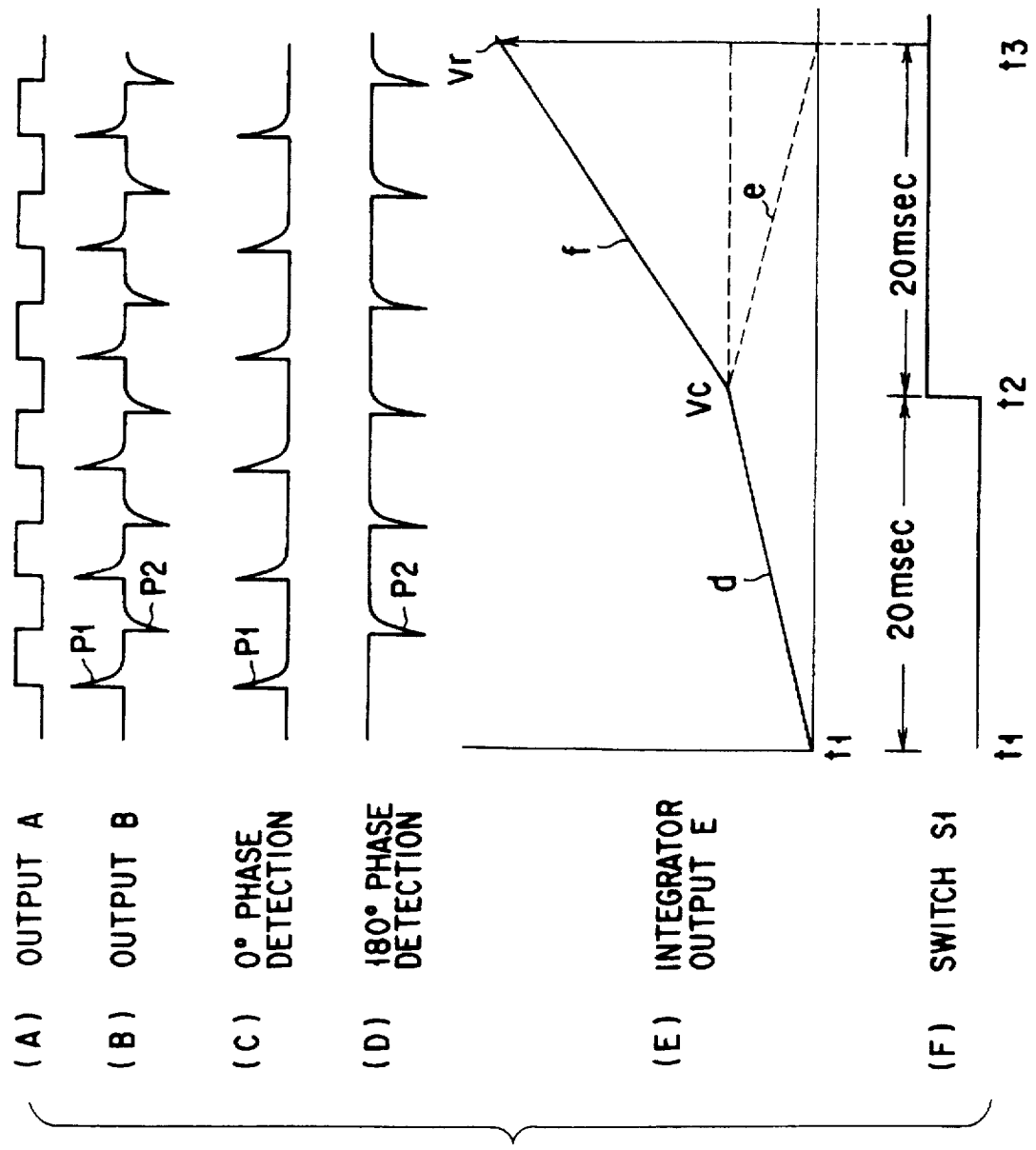
FIG. 9 is a view, showing an essential part of the timing chart of FIG. 8.

Referring then to the flowchart of FIG. 9, the principle of measuring the electric conductivity Kc of sea water will be explained. First, when the output A of the oscillator 31 has varied as is shown in FIG. 9, the coil L2 generates a saw-tooth wave B in synchronism with the leading and trailing edges of the output A. In FIG. 9, P1 represents a positive saw-tooth wave at the phase of "0"°, and P2 a negative saw-tooth wave at the phase of "180"°.

The output B of the second coil L2 is amplified by the pre-amplifier 34 to an output C as shown in FIG. 8.

For the time period from the time point t1 to the time point t2 for which the switch S1 is kept open, the switch S2 performs "0"° phase detection. In other words, the switch S2 is closed for a predetermined period of time in synchronism with the leading edge of the output A of the oscillator 31. As a result, the integrator 36 receives a positive saw-tooth wave P1 as shown in FIG. 9.

Since the integrator 36 integrates the saw-tooth wave P1, its output linearly increases as indicated by the solid line d in FIG. 9.

At the time point t2, the switch S1 is closed. Accordingly, a closed loop is formed by the electric wire 33, which consists of the one-turn third coil L3 wound on the first core 17, the one-turn fourth coil L4 wound on the second core 18 in the direction opposite to the direction of the winding of the third coil L3, and the reference resistor Rr (with the electric conductivity of Kc).

Thus, incorporating the electric wire 33 between the first and second cores 17 and 18 increases the output B of the second coil L2 as shown in FIG. 8.

This is because the electric conductivity Kr of the reference resistor Rr is set higher than the standard electric conductivity Kc of sea water. Where, for example, the resistance of the reference resistor Rr is set to 188Ω or less, and the resistance of sea water is set to a value falling within a range of from 188Ω to infinity, the electric conductivity Kr of the reference resistor Rr is higher than the electric conductivity Kc of sea water since the electric conductivity corresponds to the inverse number of the resistance.

If the switch S1 is kept open from the time point t1 to a time point t3 (i.e. the switch S1 is kept open for 40 msec.), the voltage Vc of the output of the integrator 36 at the time point t2 decreases as indicated by the broken line e as shown in FIG. 9 with the passing of time, and becomes "0" V at the time point t3, since the integrator 36 integrates the negative saw-tooth wave P2 after the time point t2. This is because the phase detection is switched to the 180° phase detection at the time point t2, and the time period from the time point t1 to the time point t2 is equal to the time period from the time point t2 to the time point t3.

In the present invention, however, at the time point t2, the phase detection is switched to the 180° phase detection and the switch S1 is closed to incorporate the electric wire 33 in the circuit. Since the electric conductivity Kr of the reference resistor Rr connected to the electric wire 33 is higher than the electric conductivity Kc of sea water, and the winding directions of the third and fourth coils L3 and L4 are opposite to each other, the voltage induced at the second coil L2 of the second core 18 is increased.

As a result, the voltage obtained by integration by the integrator 36 from the time point t2 increases as indicated by the solid line f. In the meantime, the negative saw-tooth wave P2 shown in FIG. 9 is integrated in addition to the voltage Vc obtained at the time point t2. Since, as mentioned above, the time period from the time point t1 to the time point t2 is equal to the time period from the time point t2 to the time point t3, the integrator 36 receives, from the time point t1 to the time point t3, positive saw-tooth wave P1 pulses and the same number of negative saw-tooth wave P2 pulses as the P1 pulses. Therefore, the voltage Vc already obtained by the integrator 36 at the time point t2 is reduced to "0" V at the time point t3.

As can be understood from the above, the voltage Vr obtained by the integrator 36 at the time point t3 does not depend upon the voltage Vc. In other words, the voltage Vr obtained by integration by the integrator 36 at the time point t3 is a constant voltage only proportional to the electric conductivity Kr of the reference resistor Rr which is not at all influenced by the electric conductivity Kc of sea water. Since as explained above, the reference resistor Rr is made of a material which does not require temperature compensation, the voltage Vr can be determined directly from the time period between the time points t2 and t3 and from the electric conductivity Kr of the reference resistor Rr.

Moreover, since during the time period between the time points t1 and t2, the space between the first and second cores 17 and 18 is electrically connected by means of sea water with the electric conductivity Kc introduced into the passage 15, the voltage B induced at the coil L2 of the second core 18 is proportional to the electric conductivity Kc. Accordingly, the voltage Vc which is obtained at the time point t2 as a result of integration of the voltage B from the time point t1 to the time point t2 is proportional to the electric conductivity Kc.

Further, during the time period between the time points t2 and t3, the space between the first and second cores 17 and 18 is electrically connected by means of sea water with the electric conductivity Kc introduced into the passage 15 and of the reference resistor Rr with the electric conductivity Kr.

However, since the voltage Vc obtained by the integrator 36 at the time point t2 is offset to "0" V at the time point t3, it can be considered that the voltage Vr obtained by integration by the integrator 36 at the time point t3 is proportional to the electric conductivity Kr of the reference resistor Rr.

Therefore, the following equation can be obtained:

$$Vc:Vr=Kc:Kr \quad (1)$$

The equation (1) can be modified in light of the equation Kr=S/Rr, as follows:

$$Kc=Kr*Vc/Vr=(S/Rr)(Vc/Vr) \quad (2)$$

If the output voltage A of the oscillator 31, the electromagnetic change rate of each of the first and second cores 17 and 18, the amplification factor of the amplifier 34, or the capacitance of the capacitor C1 of the integrator 36 varies, the voltage Vc is influenced by the variation and slightly varies. Since, however, the time period between the time points t1 and t2 for which the voltage Vr is measured is equal to the time period between the time points t2 and t3 for which the voltage Vc is measured, the voltage Vr is influenced in the same manner as above, and hence the influences upon the voltages Vc and Vr can be offset by virtue of the term (Vc/Vr) included in the equation (2).

Thus, the electric conductivity Kc of sea water calculated using the equation (2) is not at all influenced by a change in the output voltage A of the oscillator 31, in the electromagnetic change rate of each of the first and second cores 17 and 18, in the amplification factor of the amplifier 34, or in the capacitance of the capacitor C1 of the integrator 36.

In addition, Kr represents the electric conductivity of the reference resistor Rr which requires no temperature compensation, and therefore the electric conductivity Kc of sea water calculated using the equation (2) is not influenced by the ambient temperature or by a change, if any, in the output voltage A of the oscillator 31, in the electromagnetic change rate of each of the first and second cores 17 and 18, in the amplification factor of the amplifier 34, or in the capacitance of the capacitor C1 of the integrator 36.

The voltage Vc obtained by integration by the integrator 36 at the time point t2 is held in the sampling hold circuit 38, while the voltage Vr obtained by integration by the integrator 36 at the time point t3 is held in the sampling hold circuit 40.

The voltages Vc and Vr are supplied to the controller 32 after being converted to digital data by means of the A/D converters 41 and 42, respectively.

The controller 32 then calculates the electric conductivity Kc of sea water in the passage 15, using the equation Kc=(S/Rr)*(Vc/Vr). Thus, each time a period of 40 msec. between the time points t1 to t3 elapses, the controller 32 calculates the electric conductivity Kc.

Data indicative of the thus-obtained electric conductivity Kc is converted to serial data by the P/S converter 43, and then transmitted from the transmission circuit 44 to the personal computer installed in the survey ship S via the wire 14.

The transmission of data concerning the electric conductivity Kc is continued until the wound wire 14 is completely unwound while the probe 11 connected thereto free-falls in the ocean, and then cut because of the weight of the probe 11.

The personal computer in the surveying ship S, which receives electric conductivity Kc data every 40 msec., calculates the depth of the probe 11 in the ocean using the formula ½ gt², thereby measuring the electric conductivity Kc corresponding to the depth of the probe 11 every 40 msec.

Since as explained above, the electric conductivity of sea water is measured on the basis of electromagnetic induction, filling an epoxy resin in the core receiving portion 23b to fix the first and second cores 17 and 18 does not adversely affect the measurement.

Moreover, the portions of the probe 11 to be brought into contact with sea water are made of borosilicate glass 21c and an epoxy resin 20 which have extremely low thermal expansion coefficients and which are electrochemistry stable materials. Therefore, no electric corrosion will appear even after long use in sea water.

Since borosilicate glass is provided on the inner periphery of the passage 15, the inner diameter of the passage 15 can be kept constant irrespective of a change in the pressure or temperature of sea water. As a result, the accuracy of the measured electric conductivity can be further enhanced.

Although in the conventional electrode-type electric conductivity measurement apparatus, a measurement error will occur until the electrodes are adapted to sea water, the present invention is free from such a measurement error since the first and second cores 17 and 18 do not contact sea water.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. An electric conductivity measurement circuit comprising:

first and second cores for forming a closed flux loop in a liquid whose electric conductivity is to be measured;

a first coil wound on the first core, and a second coil wound on the second core in a direction opposite to the direction of the winding of the first coil;

an oscillator for supplying voltage pulses to the first coil of the first core;

a phase detection circuit for detecting the phase of a voltage induced at the second coil of the second core;

a closed circuit including a third coil wound on the first core, a fourth coil wound on the second core in a direction opposite to the direction of the winding of the third coil, a reference resistor Rr and switch means;

an integration circuit for integrating outputs from the phase detection circuit;

first and second sampling hold circuits for holding output signals from the integration circuit, respectively, and control means for periodically turning on and off the switch means and calculating the electric conductivity Kc of the liquid.

2. The measurement circuit according to claim 1, wherein the electric conductivity calculating means is housed in a lower tip end portion of a probe, and the first and second cores are opposed to each other along the axis of the probe with an axial passage interposed therebetween, the passage being formed in the tip end portion of the probe for introducing the liquid.

3. The method of calculating an electric conductivity of a liquid in an electric conductivity measurement circuit which has a first coil wound on a first core, a second coil wound on a second core, a closed circuit including the first and second coils, a reference resistor and switch means, comprising:

periodically turning on and off a second switch means, thereby detecting a voltage induced at a second coil in synchronism with a leading edge of a voltage pulse while a first switch means is in an off period;

integrating voltages induced at the second coil;

holding in a first sample hold circuit a voltage Vc output from the integration circuit as a result of integration performed until the off period terminates;

detecting a voltage induced at the second coil in synchronism with the trailing edge of each voltage pulse while said first switch means is in an on period;

integrating voltages induced at the second coil in the on periods;

holding in a second sample hold circuit a voltage Vr output from the integration circuit as a result of integration performed until the on period terminates; and calculating the electric conductivity Kc of the liquid using the equation $Kc = (S/Rr)(Vc/Vr)$, where S represent a cell constant which depends upon the configuration of a cell and Rr is the reference resistor.

* * * * *